US008974538B2

(12) United States Patent
Teeny et al.

(10) Patent No.: US 8,974,538 B2
(45) Date of Patent: Mar. 10, 2015

(54) ORTHOPEDIC SPACER

(71) Applicants: Steven M. Teeny, Gig Harbor, WA (US); Barry M. Fell, Hummelstown, PA (US)

(72) Inventors: Steven M. Teeny, Gig Harbor, WA (US); Barry M. Fell, Hummelstown, PA (US)

(73) Assignee: Steven M. Teeny, Gig Harbor, WA (US)

( * ) Notice: Subject to any disclaimer, the term of this patent is extended or adjusted under 35 U.S.C. 154(b) by 28 days.

(21) Appl. No.: 13/843,357

(22) Filed: Mar. 15, 2013

(65) Prior Publication Data

US 2014/0277532 A1  Sep. 18, 2014

(51) Int. Cl.
A61F 2/38 (2006.01)
A61F 2/28 (2006.01)
A61B 17/56 (2006.01)

(52) U.S. Cl.
CPC ..................................... *A61F 2/3836* (2013.01)
USPC .................. 623/20.24; 623/16.11; 623/20.14; 623/20.15; 623/20.21; 606/60

(58) Field of Classification Search
CPC .................................................... A61F 2/3836
USPC .......... 623/13.12, 16.11, 20.12, 20.14, 20.24, 623/20.28, 20.32, 20.35, 23.36, 23.39, 623/23.47; 606/60, 62, 88, 90, 105; 27/21.1
See application file for complete search history.

(56) References Cited

U.S. PATENT DOCUMENTS

| 4,502,160 | A | | 3/1985 | Moore |
| 4,938,768 | A | * | 7/1990 | Wu ............................. 623/23.47 |
| 6,019,794 | A | | 2/2000 | Walker |
| 6,053,945 | A | * | 4/2000 | O'Neil et al. .............. 623/20.32 |
| 6,245,111 | B1 | | 6/2001 | Shaffner |
| 6,569,203 | B1 | | 5/2003 | Keller |
| 6,953,479 | B2 | | 10/2005 | Carson |
| 7,427,296 | B2 | | 9/2008 | Evans |
| 8,097,039 | B2 | | 1/2012 | Evans |
| 2003/0040805 | A1 | | 2/2003 | Minamikawa |
| 2006/0229732 | A1 | | 10/2006 | Bachelier |
| 2007/0179609 | A1 | | 8/2007 | Goble |
| 2008/0306603 | A1 | | 12/2008 | Reich |
| 2009/0076606 | A1 | * | 3/2009 | Huerta et al. .............. 623/16.11 |
| 2009/0171463 | A1 | * | 7/2009 | Brehm ....................... 623/20.14 |
| 2010/0042214 | A1 | | 2/2010 | Nebosky |

(Continued)

OTHER PUBLICATIONS

Haddad, F.S., et al., "The PROSTALAC Functional Spacer in Two-Stage Revision for Infected Knee Replacements," Journal of Bone and Joint Surgery: British vol. 82-B(6):807-812, Aug. 2000.

Moyad, T.F., et al., "Evaluation and Management of the Infected Total Hip and Knee," Orthopedics 31(6):581-590, Jun. 2008.

(Continued)

*Primary Examiner* — Thomas J Sweet
*Assistant Examiner* — Christie Bahena
(74) *Attorney, Agent, or Firm* — Christensen O'Connor Johnson Kindness PLLC

(57) ABSTRACT

A temporary knee replacement assembly and kit includes a tibial plate that attaches to the tibia, a tibial rod that extends through the plate into the medullary cavity and abuts the plate. A femoral plate attaches to the femur, and a femoral rod extends through the second plate into the femur medullary cavity and abuts the plate. A locking spacer connects the two rods. The spacer may be length adjustable or may be provided in multiple sizes for length selection. One or both of the rods may include a bone cement/antibiotic coating to provide antibiotic treatment to the tissue. The kit may include multiple tibial and femoral rods, multiple tibial and femoral plates, and multiple locking spacers, to accommodate different applications.

19 Claims, 13 Drawing Sheets

(56) References Cited

U.S. PATENT DOCUMENTS

2010/0217401 A1* 8/2010 de Beaubien ............ 623/20.34
2010/0312350 A1 12/2010 Bonutti
2011/0208315 A1* 8/2011 Anapliotis et al. ......... 623/20.24
2011/0313532 A1 12/2011 Hunt
2012/0022664 A1 1/2012 Vander Meulen

OTHER PUBLICATIONS

Siebel, T., et al., "Two-Stage Exchange of Infected Knee Arthroplasty With an Prosthesis-Like Interim Cement Spacer," Acta Orthopaedica Belgica 68(2):150-156, Apr. 2002.

International Search Report and Written Opinion mailed Jun. 3, 2014, issued in corresponding International Application No. PCT/US2014/020407, filed Mar. 4, 2014, 12 pages.

* cited by examiner

ORTHOPEDIC SPACER

BACKGROUND

Total joint replacement, a surgical procedure wherein a damaged joint is removed and replaced with a new prosthetic joint, has become increasingly common due to a growing need for joint replacement and to improvements in artificial joint technology, arthroplasty surgical techniques, and post-operative treatment regimens. It has been estimated that in the U.S. alone, approximately one million hip or knee total joint replacement surgeries are performed annually. The Agency for Healthcare Research and Quality reported that more than 600,000 total knee replacements are performed each year in the United States.

Arthritis is the most common cause of chronic knee pain and disability. A 2010 study by the Center for Disease Control and Prevention reports that 50 million U.S. adults had arthritis in 2007-2009, an increase of about 9% from 2003-2005. Osteoarthritis, rheumatoid arthritis, and post-traumatic arthritis are the most prevalent forms of arthritis, resulting in chronic knee pain. Non-surgical treatments, such as anti-inflammatory medications, cortisone injections, lubricating injections, physical therapy, and the like, are typically undertaken to improve joint function and to diminish pain. If non-surgical treatments are not successful, total joint replacement may be indicated.

In a typical knee joint replacement procedure, the femur and tibia are first prepared by removing the damaged cartilage surfaces along with a small amount of bone. Metal implants are then cemented to the ends of the femur and tibia. Optionally, the patella may be resurfaced. Then a spacer, generally a medical-grade plastic spacer, is inserted between the metal components.

Total knee replacements have been called one of the most successful procedures in medicine, with upwards of 90% of patients having total knee replacement surgery reporting significant reduction of knee pain and improvements in ability to perform normal daily tasks. The complication rate following total knee replacement surgery is low. Serious complications such as knee joint infection occur at rates that have been reported in the range of 1% and 3%.

Although an infected prosthetic knee is sometimes removed and replaced with a new prosthesis in a single operation, greater success at curing the infection has been achieved using a two-stage surgical procedure. In the first stage the infected prosthesis is removed and replaced with a temporary, antibiotic-infused cement spacer which is left in vivo between the femur and the tibia, typically for several weeks. The classic way a cement spacer has been made is to combine bone cement powder, antibiotics, and a monomer to form a doughy cement that is placed into the knee space and allowed to harden with the leg extended, and then closing the wound. The antibiotic in the spacer leaches out over time to treat the infection. More recent spacers or temporary joints provide additional support structure. The temporary spacer may be a static spacer or may be articulated, to allow flexure of the knee joint. In the second stage the temporary spacer is removed, and a permanent total knee prosthesis is implanted. An example of a first stage spacer is disclosed in U.S. Pat. No. 8,097,039, to Evans, the disclosure of which is hereby incorporated by reference.

One problem with conventional static spacers is that the antibiotic cement placed into the defect formed by the removal of the artificial knee may not provide sufficient stability to the joint. Even though the joint is not intended to move, voluntary or involuntary muscle contractions can cause motion in the joint, which may be painful and could damage the fragile bone further. One way to support the joint is to install an intra-medullary rod extending between the tibia and femur, and cementing it with bone glue so that the bones cannot move. However, it may be difficult to place the intra-medullary rod between the two bones, as the procedure requires first sliding the intra-medullary rod far up into the medullary cavity of one bone, and then repositioning (extending) the joint and moving the rod back into the medullary cavity of the other bone, such that the rod is disposed in both medullary cavities and spans the gap therebetween. This procedure may contaminate the medullary cavity further, and carry bone glue further into the bone than is desired. It can also be very difficult to remove the rod.

There remains a need for improvements to first stage spacers or temporary joint replacements that are more easily installed, provide improved joint stability, provide antibiotic treatment deep into the tissue, and are adjustable to accommodate particular patients and procedures.

SUMMARY

This summary is provided to introduce a selection of concepts in a simplified form that are further described below in the Detailed Description. This summary is not intended to identify key features of the claimed subject matter, nor is it intended to be used as an aid in determining the scope of the claimed subject matter.

A temporary knee replacement, or orthopedic spacer, suitable for replacing a total knee replacement assembly that has become infected, includes a tibial plate that is sized to engage the proximal end of the tibia at the knee joint, and a femoral plate that is sized to engage the distal end of the corresponding femur. A tibial rod having an elongate portion which may optionally be treated with an antibiotic coating, is inserted into the tibia medullary cavity, and is stopped by the tibial plate. An end portion of the tibial rod defines a transverse channel, for example a C-shaped channel, on its proximal end. A femoral rod similarly includes an elongate portion which may optionally be treated with an antibiotic coating, and is inserted into the femur medullary cavity, where it is stopped by the femoral plate. The femoral rod defines a transverse channel on its distal end. A locking spacer includes a first slide portion on one side that slidably engages the tibial rod channel and a second slide on the opposite side that slidably engages the femoral rod channel, thereby joining the tibial rod to the femoral rod. The locking spacer is fixed to the rods with suitable fasteners. In one embodiment the fasteners extend through an attachment plate portion of the locking spacer.

In an embodiment, the tibial plate and/or the femoral plate includes projections, for example tapered posts or supports, that engage the ends of the bone, and help to fix the location of the plates.

In an embodiment, the channels are C-shaped, and the slides are arcuate to slidably engage the C-shaped channels.

In an embodiment, the locking spacer further comprises a threaded aperture or other means to aid in removing the locking spacer to facilitate removal of the temporary knee replacement.

In an embodiment, the rods are provided with an antibiotic coating comprising a mixture of antibiotic, bone cement powder, and a monomer, wherein the mixture is molded onto the elongate portions of the rods.

In an embodiment, the locking spacer is selected from a plurality of locking spacers having differing lengths.

In another aspect of the invention, a temporary knee replacement is provided in a kit form comprising a plurality of femoral and tibial rods having differing lengths, a plurality of femoral and tibial plates having differing sizes, and a plurality of locking spacers providing differing spacing between the first and second slides. The kit may further comprise a plurality of covers, each cover associated with one of the plurality of locking spacers. The kit may further comprise an antibiotic composition and/or fasteners for fixing the selected rods to the selected locking spacer.

In another aspect of the invention, a method for temporarily immobilizing a knee portion of a leg having an infected artificial knee comprises: (i) removing the infected artificial knee from the associated femur and tibia; (ii) inserting an elongate portion of a femoral rod through an aperture in a femoral plate and into the femur medullary cavity such that the femoral plate is disposed on an end of the femur and an end portion of the femoral rod abuts the femoral plate, wherein the femoral rod end portion defines a first C-shaped channel; (iii) inserting an elongate portion of a tibial rod through an aperture in a tibial plate and into the tibia medullary cavity such that the tibial plate is disposed on an end of the tibia and an end portion of the tibial rod abuts the tibial plate, wherein the tibial rod end portion defines a second C-shaped channel; (iv) connecting the femoral rod to the tibial rod with a locking spacer having a first slide portion that engages the first channel and a second slide portion that engages the second channel; and (v) installing a first fastener that fixes the locking spacer to the femoral rod and installing a second fastener that fixes the locking spacer to the tibial rod.

In an embodiment, the method further comprises applying an antibiotic composition about the locking spacer.

In an embodiment, the locking spacer further comprises an attachment plate portion that receives the first and second fasteners, and further comprises installing a snap-fit cover over the attachment plate portion.

In an embodiment, the method further comprises selecting the locking spacer from a plurality of locking spacers provided in a kit, wherein each of the plurality of locking spacers has a different spacing length such that the distance between the femoral rod and the tibial rod is determined by the selected locking spacer.

In another aspect a temporary knee replacement comprises a tibial component comprising an elongate rod configured to be inserted into a tibia medullary cavity and having a proximal end portion defining a first channel, the tibial component further comprising an outwardly-extending plate portion disposed between the elongate rod and the proximal end portion, wherein the plate portion is configured to engage a proximal end of the tibia; a femoral component comprising an elongate rod configured to be inserted into a femur medullary cavity and having a distal end portion defining a second channel, the femoral component further comprising an outwardly-extending plate portion disposed between the elongate rod and the distal end portion, wherein the plate portion is configured to engage a distal end of the femur; a locking spacer comprising (i) a first slide portion that is shaped to slidably engage the first channel such that the first slide portion is restrained from moving within the first channel except along the first channel, (ii) a second slide portion that is shaped to slidably engage the second channel such that the second slide portion is restrained from moving within the second channel except slidably along the second channel, and (iii) an attachment plate portion; and a first fastener configured to fix the position of the first slide portion in the first channel and a second fastener configured to fix the position of the second slide portion in the second channel.

DESCRIPTION OF THE DRAWINGS

The foregoing aspects and many of the attendant advantages of this invention will become more readily appreciated as the same become better understood by reference to the following detailed description, when taken in conjunction with the accompanying drawings, wherein.

DETAILED DESCRIPTION

Figure 1:
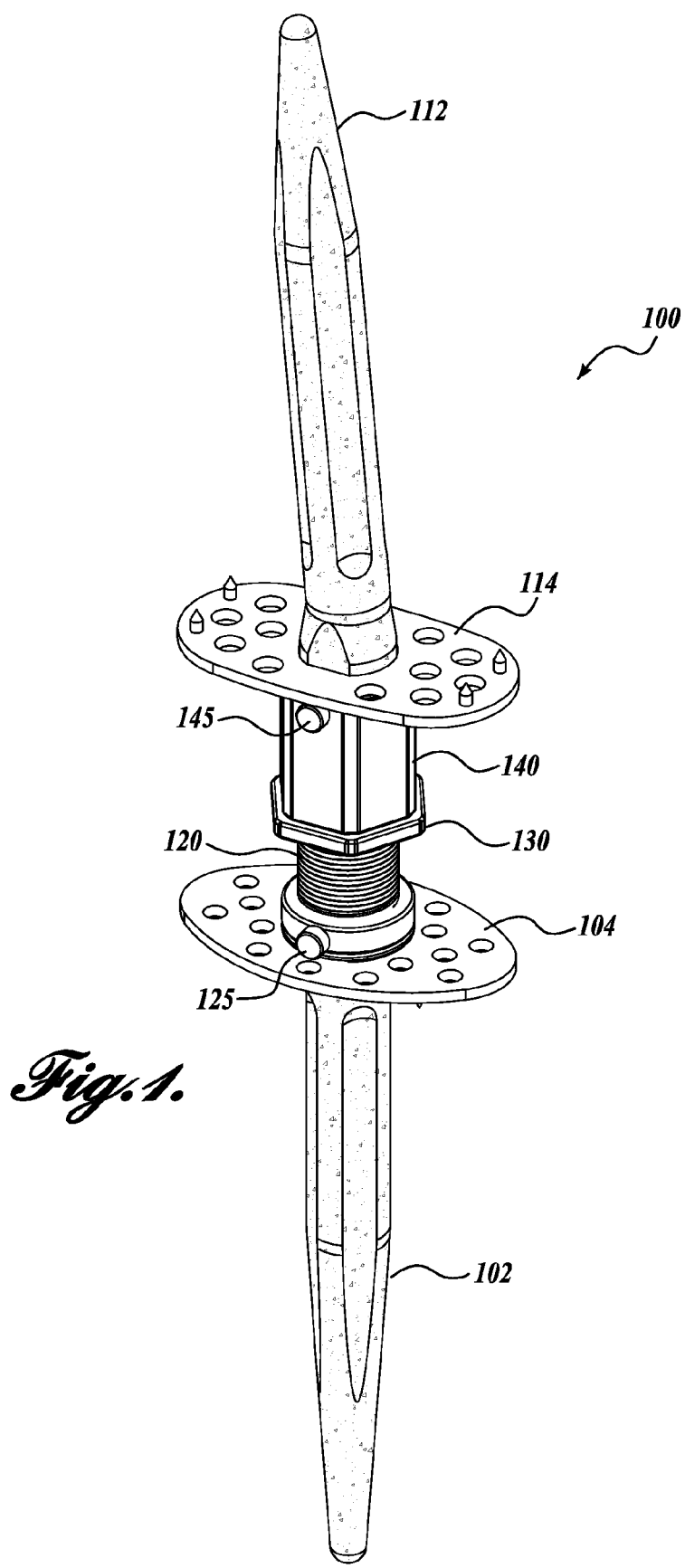
FIG. 1 is a perspective view of a temporary knee replacement assembly in accordance with the present invention.
Figure 2:
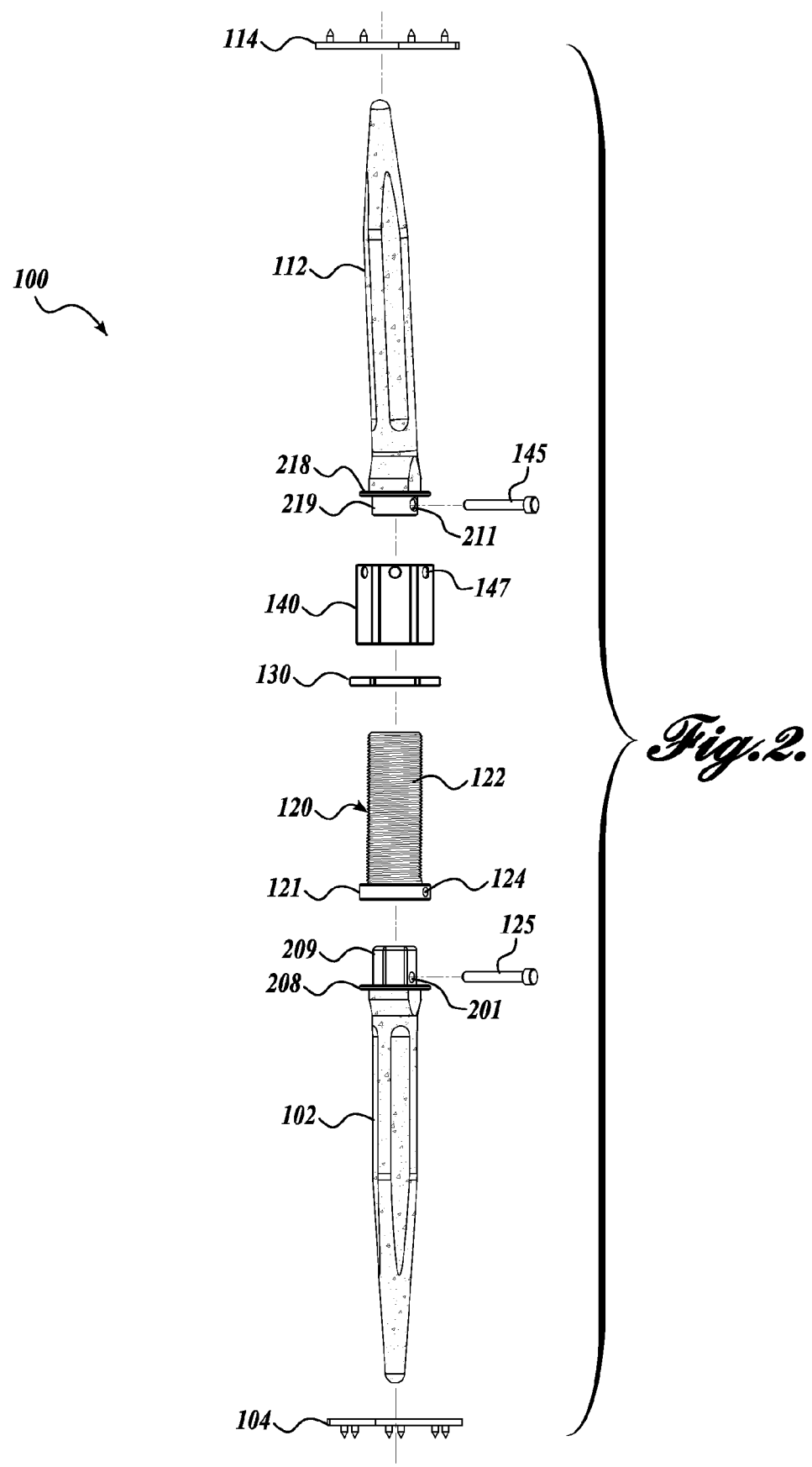
FIG. 2 is an exploded view of the temporary knee replacement assembly shown in FIG. 1.

A temporary joint replacement assembly, kit, and method will now be described with reference to a temporary knee replacement ("TKR"), although it will be readily apparent to persons of skill in the art that the teachings herein may be applied to other joints. Current embodiments of a TKR assembly 100 in accordance with the present invention is described with reference to the Figures, wherein like numbers indicate like parts. A perspective view of a first embodiment of a TKR assembly 100 is shown in FIG. 1, and an exploded view is shown in FIG. 2. The TKR assembly 100 is designed to temporarily replace an infected artificial knee, and provide an antibiotic treatment deep into the tissue while the TKR assembly 100 is in place. For example, the TKR assembly 100 might be implanted into an infected joint and bones, and remain in place for 3-8 weeks. The TKR assembly 100 is then removed and replaced with a permanent artificial knee.

In this embodiment, the TKR assembly 100 includes: (i) a tibial rod 102 that is configured to be inserted deep into the medullary cavity of a tibia or shin bone; (ii) a tibial plate 104 configured to abut an upper end of the tibia; (iii) an externally threaded member 120 that is attached to the tibial rod 102 with a first pin 125; (iv) a locking nut 130; (v) an internally threaded member 140 configured to threadably engage the externally threaded member 120; (vi) a femoral plate 114 configured to abut a lower end of a thigh bone or femur; and (vii) a femoral rod 112 that is attached to the internally threaded member 140 with a second pin 145 and is configured to be inserted deep into the medullary cavity of the femur.

The TKR assembly 100 is configured to implant a tibial subassembly into the tibia, and a femoral subassembly into the femur. The two subassemblies are then assembled and adjusted to provide a desired spacing. The tibial subassembly includes the tibial plate 104, the tibial rod 102, the externally threaded member 120, the locking nut 130, and the internally threaded member 140. The femoral subassembly includes the femoral plate 114 and the femoral rod 112. The two subassemblies may be readily implanted or installed with the tibia and femur disposed in a flexed position. The leg may then be manipulated to an extended position, to allow the distal end of the femoral rod 112 to be inserted into the proximal end of the internally threaded member 140. The internally threaded member 140 may then be rotated to adjust the spacing between the tibial rod 102 and the femoral rod 112. For example, in the current embodiment, the internally threaded member 140 is hexagonal in cross section to facilitate rotating the member 140 to adjust the spacing. The lock nut 130 is then tensioned, and the second pin 145 is inserted to lock the assembly 100 in the desired adjustment.

Figure 3:
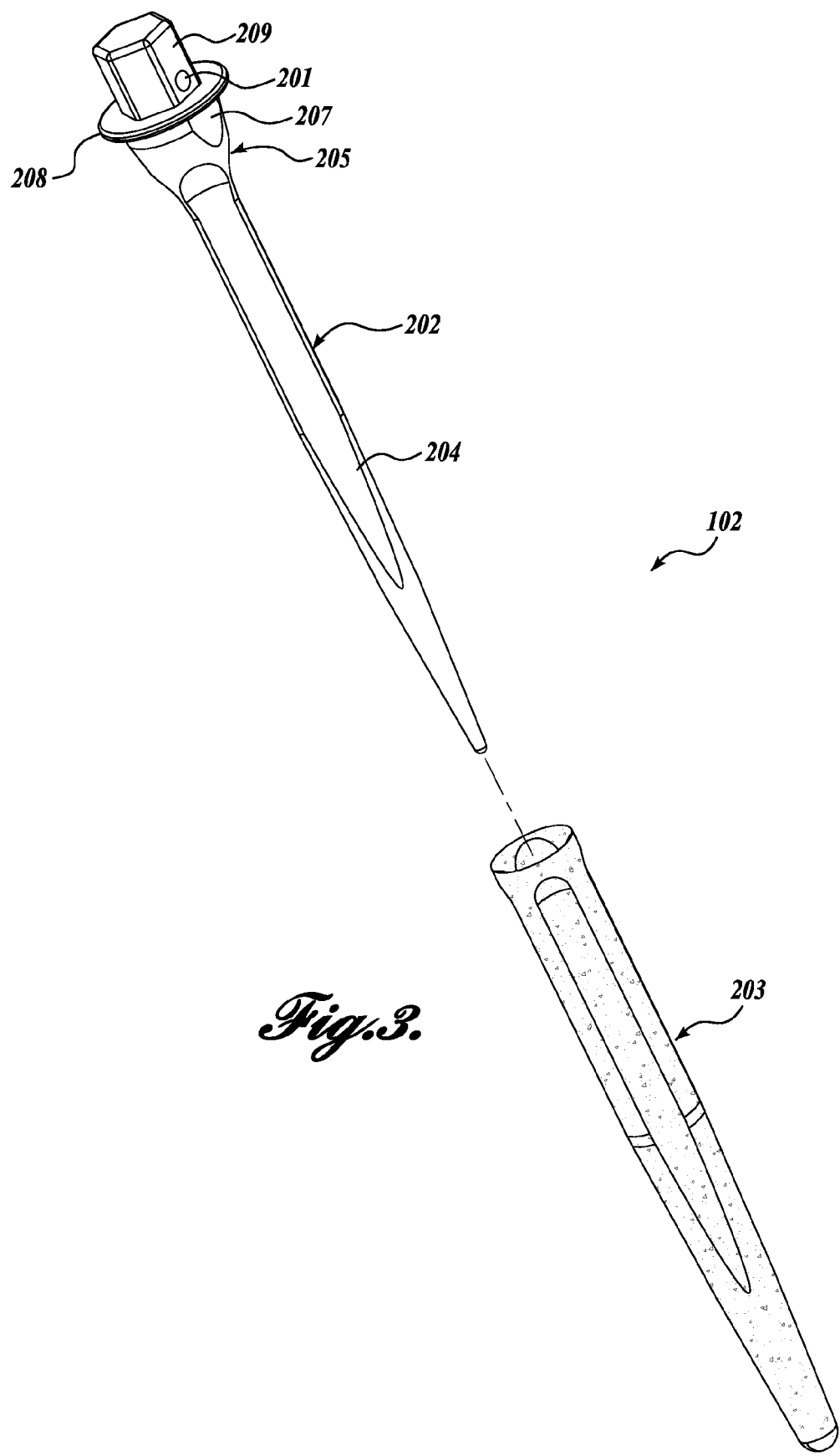
FIG. 3 is a partially exploded view of the tibial rod for the temporary knee replacement assembly shown in FIG. 1.

An exploded perspective view of the tibial rod 102 is shown in FIG. 3. The tibial rod 102 comprises a nail portion 202, which may be formed from any suitable biocompatible material. The nail portion 202 and the other components of the TKR assembly 100 may be formed, for example, from a biocompatible metal such as stainless steel, titanium, or the like. The tibial rod 102 also includes a coating or covering 203 of an antibiotic impregnated material, for example an antibiotic bone cement. Other antimicrobial coatings may also or alternatively be applied, including for example, silver plating or the like.

The nail portion 202 includes a tapered shaft 204 that extends distally from a head portion 205. The tapered shaft 204 receives and supports the antibiotic bone cement coating 203. The head portion 205 comprises a shaped distal post 207, a flange 208, and a shaped proximal post 209. The proximal post 209 has a transverse aperture 201 therethrough. For example, in the current embodiment, the shaped proximal post 209 is hexagonal.

Figure 4:
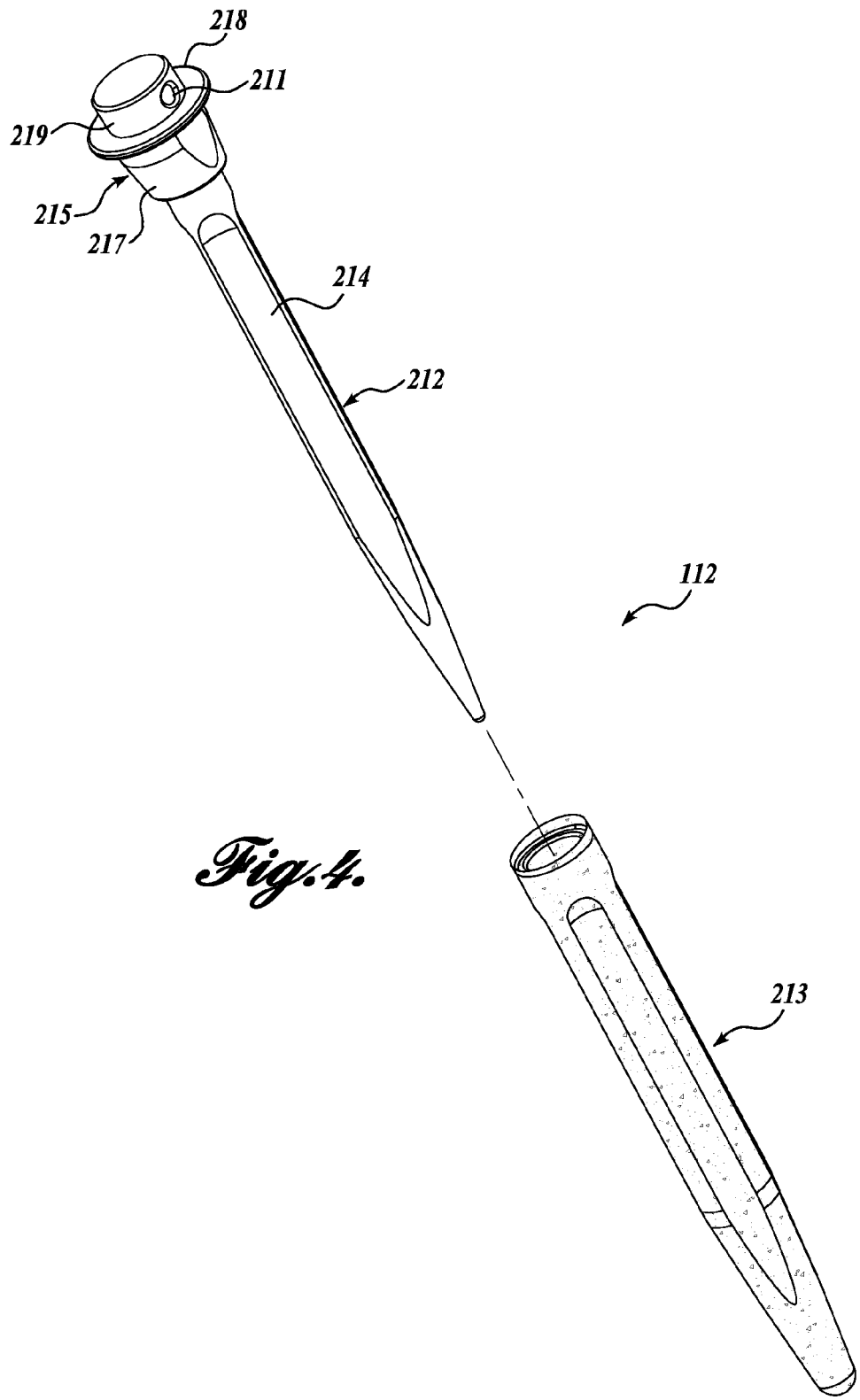
FIG. 4 is a partially exploded view of the femoral rod for the temporary knee replacement assembly shown in FIG. 1.

An exploded perspective view of the femoral rod 112 is shown in FIG. 4. The femoral rod 112 comprises a nail portion 212, which may be formed, for example, from the same biocompatible material as the tibial nail portion 202. A coating or covering 213 of an antibiotic impregnated material, for example an antibiotic bone cement portion is also provided.

The nail portion 212 includes a tapered shaft 214 that extends distally from a head portion 215. The head portion 215 comprises a shaped post 217, a flange 218, and a cylindrical post 219. A transverse aperture 211 extends through the cylindrical post 219. The tapered shaft 214 is preferably angled (e.g., relative to the head portion 215) to approximately correspond to the angle of the femur medullary cavity.

The antibiotic cement may comprise one or a combination of more than one antibiotic or other antimicrobial agent(s). Exemplary antibiotics include aminoglycoside antibiotics, for example tobramycin, glycopeptide antibiotics, for example vancomycin, or the like. The antibiotic(s) are stabilized in a bone cement, such that after implantation a portion of the antibiotic will gradually elute or otherwise release from the antibiotic cement 203 to treat the infected tissue.

Figure 5:
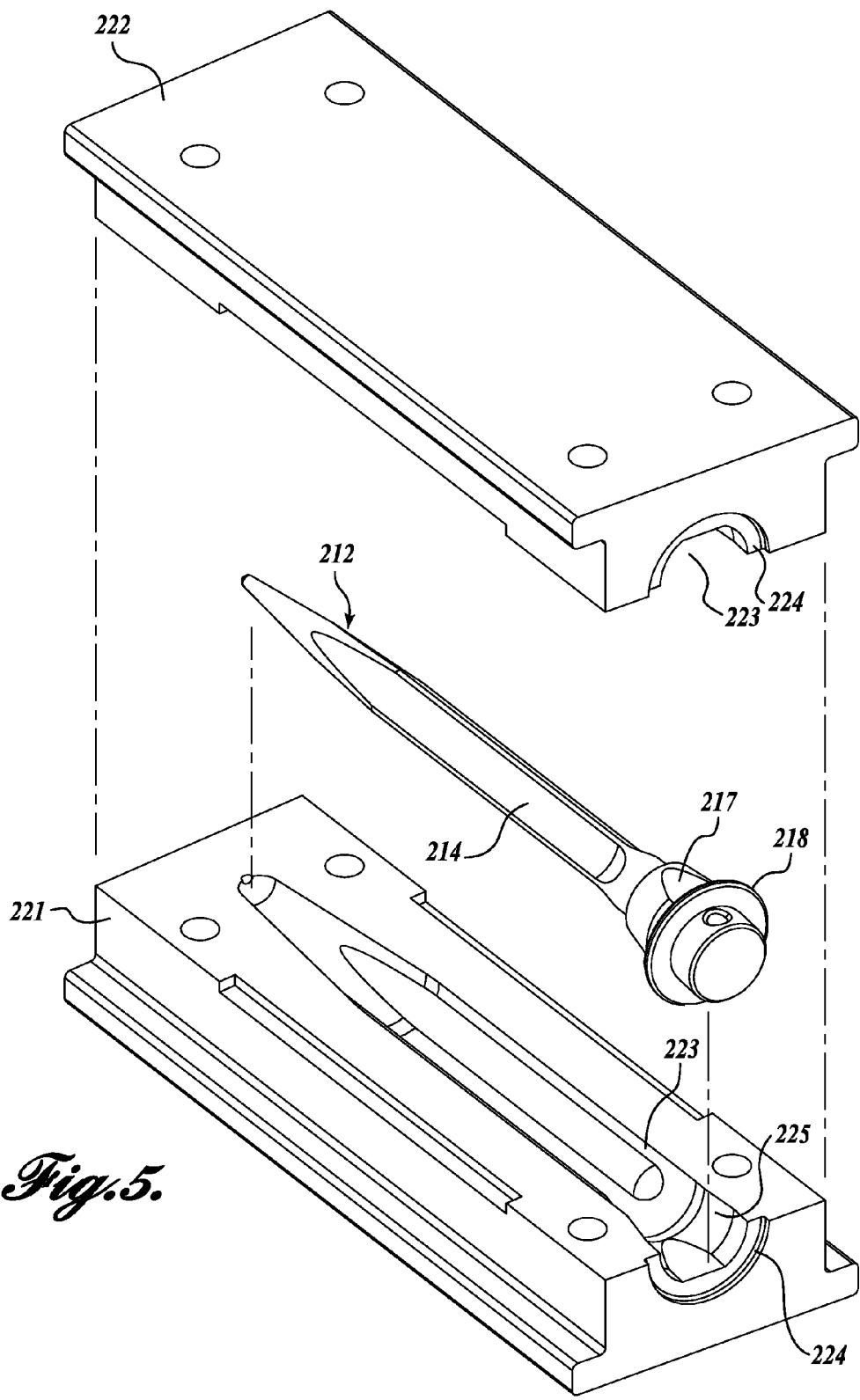
FIG. 5 illustrates a mold for forming an antibiotic coating onto the tapered shaft on the nail portion of the femoral rod shown in FIG. 1.

The antibiotic cement coatings 203, 213 may be applied to the nail portions 202, 212, respectively, in any suitable manner. For example, a split mold for forming an antibiotic cement coating on the femoral nail portion 212 is shown in FIG. 5. The split mold includes a first mold body 221 and a second mold body 222 that cooperatively define a recess 223 that is designed to receive the nail portion 212 with the tapered shaft 214 approximately centered in the recess 223. A lower recess portion 225 is configured to receive the shaped post 217, and an end recess 124 is configured to receive the flange 218.

The antibiotic cement may be mixed, and then applied or molded in a layer on the recess 223 on both mold bodies 221, 222. The femoral nail portion 212 is then placed on one of the mold bodies 221, 222 with the flange 218 disposed in the end recess 224. The other mold body 222, 221 is placed over the first, and the antibiotic cement is allowed to set. The tibial rod 102 may be similarly formed.

Other methods for applying an antibiotic cement to the nail portions 202, 212 are contemplated. For example, the antibiotic cement may be injected into a mold containing the nail portions, or hand-formed or machine-formed directly onto the nail portions.

Figure 6:
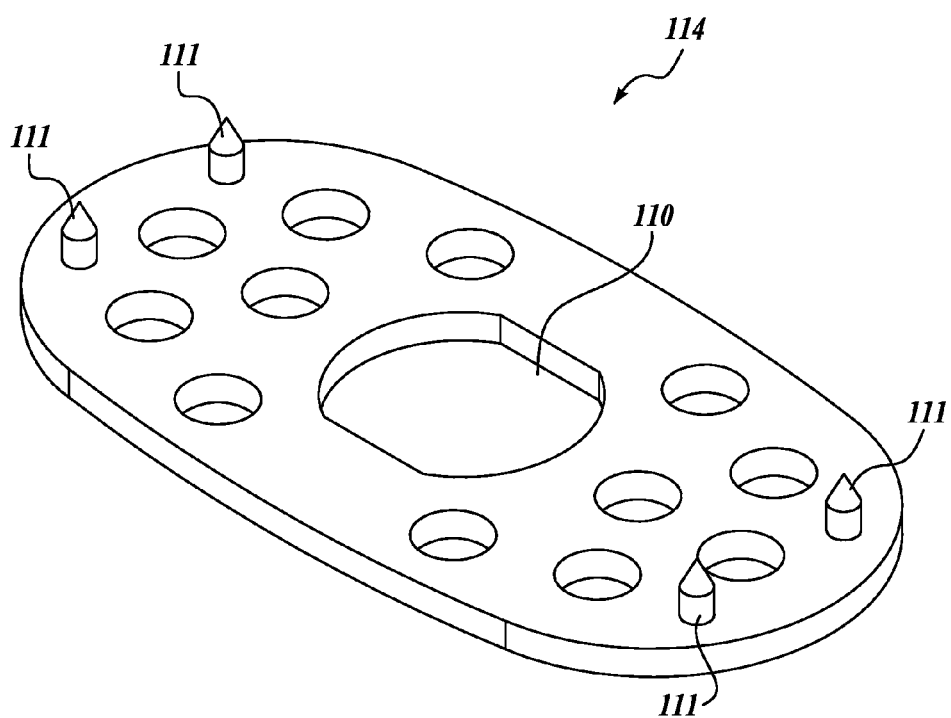
FIG. 6 is a perspective view of the femoral plate for the temporary knee replacement assembly shown in FIG. 1.

A perspective view of the femoral plate 114 is shown in FIG. 6. The femoral plate 114 is configured to engage the distal end of the femur to locate and stabilize the implanted femoral rod 112. The femoral plate 114 has a shaped aperture 110 that is sized and configured to engage the shaped post 217. The bone side of the femoral plate 114 may include tapered posts 111 or other features to engage the femur and retain the femoral plate 114 at the desired position. The femoral rod 112 may be inserted into the femoral plate 114 and inserted into the femur's medullary cavity until the plate 114 abuts the femur and the flange 218 abuts the femoral plate 114. The femoral plate 114 therefore establishes the depth that the femoral rod 112 can be inserted into the medullary cavity and prevents the rod 112 from rotating after it is inserted.

The tibial plate 104 is generally similar in shape and function to the femoral plate 114, and configured to engage the tibia over the tibial medullary cavity. It is contemplated that the tibial and femoral plates 104, 114 may be provided in a plurality of shapes and/or sizes such that the optimal plates may be selected to meet the needs of a particular patient and procedure.

Figure 7:
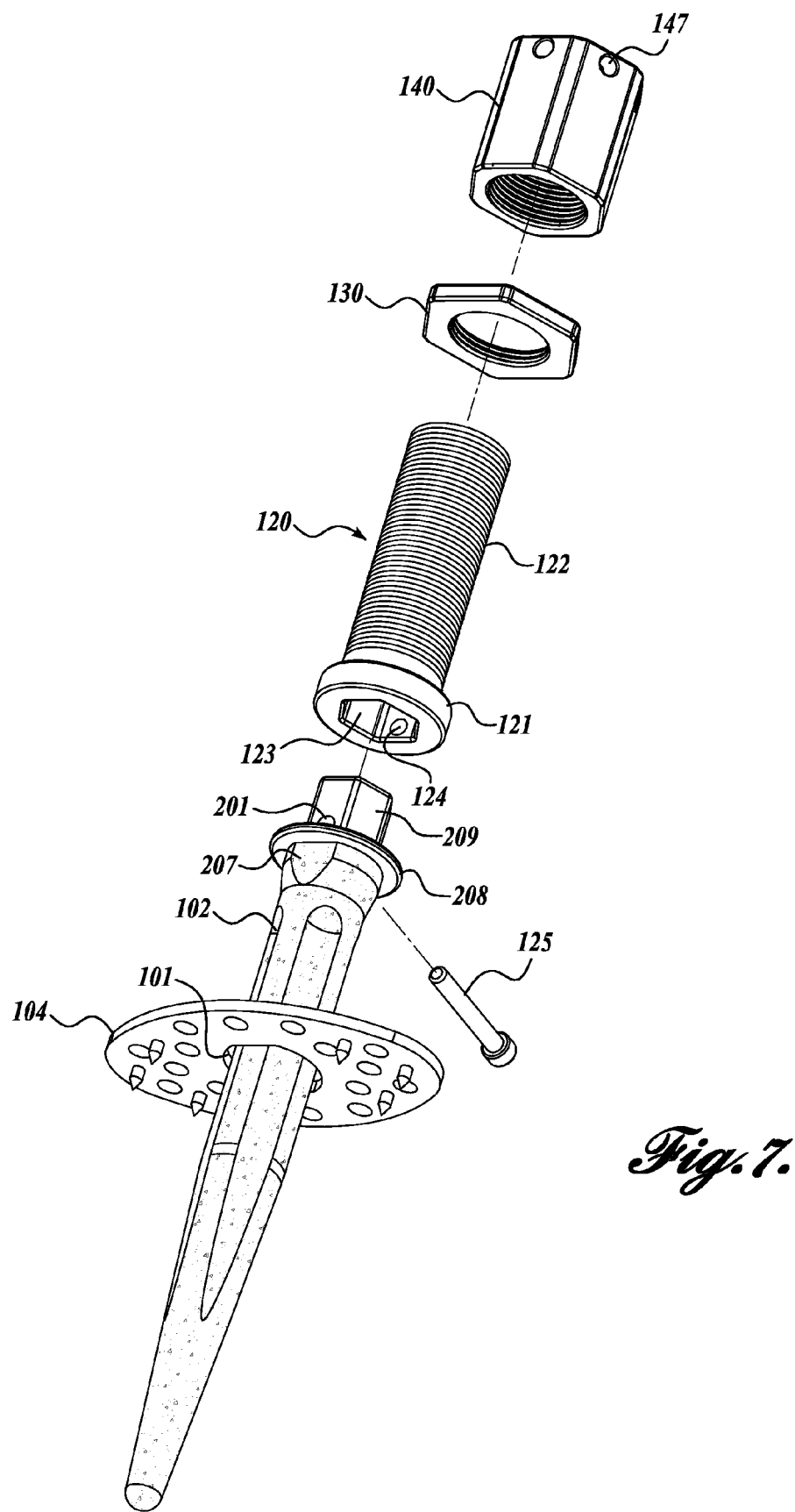
FIG. 7 is an exploded view of the tibial subassembly of the temporary knee replacement assembly shown in FIG. 1.

A partially exploded view of a tibial subassembly of the TKR assembly 100 is shown in FIG. 7. The tibial plate 104 is configured to attach to the tibia over the medullary cavity. It is contemplated that the desired location and orientation of the tibial plate 104 will be determined prior to surgery. The tibial rod 102 is inserted through the shaped aperture 101 in the tibial plate 104, such that the correspondingly shaped distal post 207 engages the shaped aperture 101 and the flange 208 abuts the tibial plate 104. The insertion depth and rotational orientation of the tibial rod 102 is therefore fixed by the positioning of the tibial plate 104.

The externally threaded member 120 includes a head 121 with a shaped recess 123, and an elongate threaded portion 122. The shaped recess 123 is configured to receive the correspondingly shaped proximal post 209 on the tibial rod 102. A transverse aperture 124 through the head 121 is positioned to be aligned with the transverse aperture 201 in the shaped post 209 when it is fully inserted. The locking pin 125 is then inserted through both transverse apertures 124, 201 to axially lock the externally threaded member 120 to the tibial rod 102. The locking nut 130 is threaded over the threaded portion 122. The internally threaded member 140 is threaded onto the threaded portion 122, such that the proximal end extends beyond the threaded portion 122.

Figure 8:
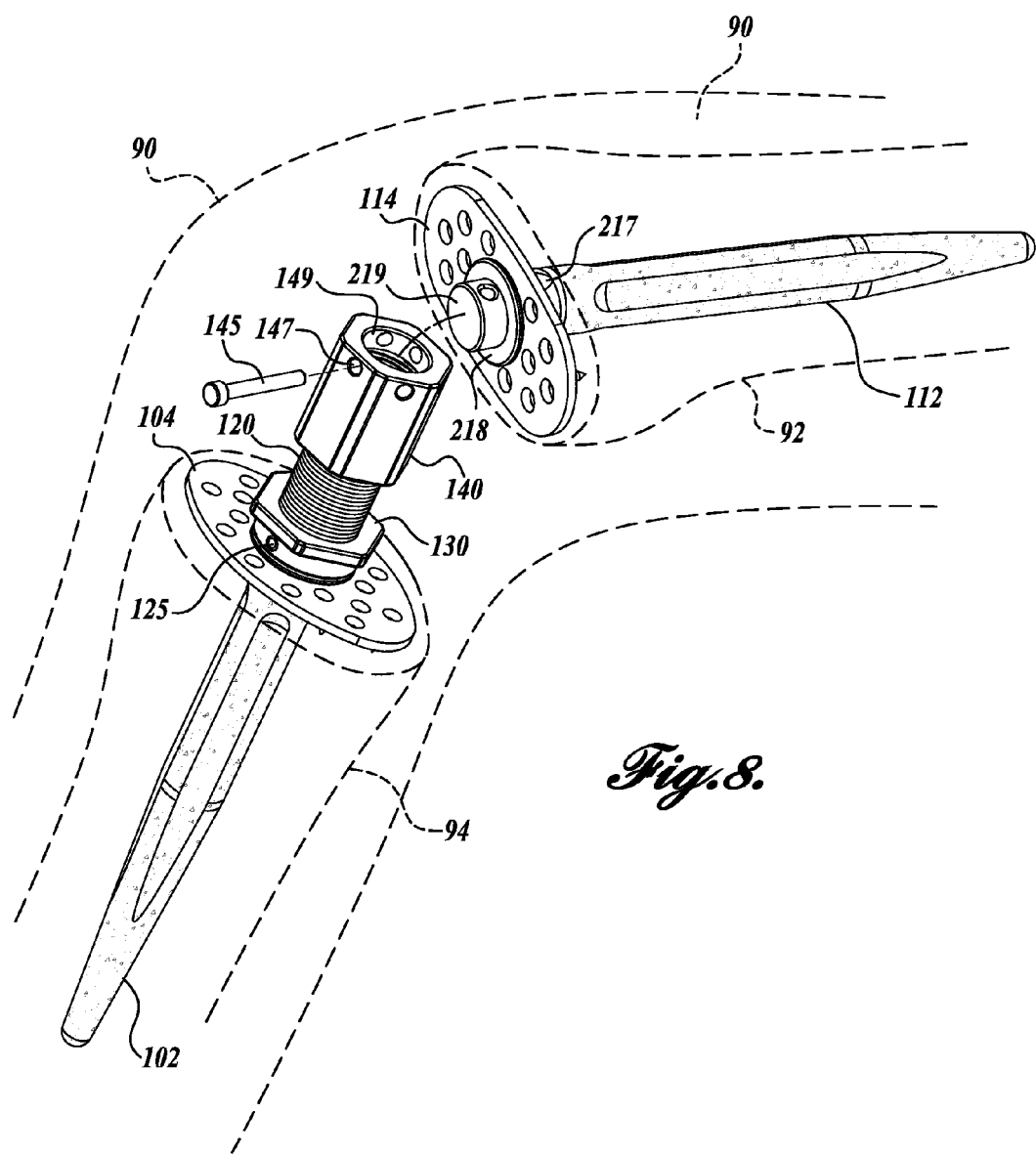
FIG. 8 illustrates joining the tibial and femoral subassemblies for the temporary knee replacement assembly shown in FIG. 1.

FIG. 8 illustrates joining the femoral subassembly with the tibial subassembly in a leg 90. The femoral rod 112 may be inserted through the aperture in the femoral plate 114 and inserted into the medullary cavity. The femoral plate 114 attaches to the femur 92, and the femoral rod 112 flange 218 abuts the femoral plate 114. The internally threaded member 140 defines a proximal cylindrical recess 149 that is sized to receive the cylindrical post 219 on the femoral rod 112. One or more transverse apertures 147 extend through the member 140 at the cylindrical recess 149, and the femoral rod 112 is locked to the internally threaded member with the second pin 145.

In one embodiment, the steps for installing the TKR assembly 100, after removal of an existing total knee replacement, debridment of the wound, preparation of the site, and preparing and applying the antibiotic cement comprise: (i) attaching the tibial plate 104 to the tibia 94; (ii) inserting the tibial rod 102 into the tibia medullary cavity through the tibial plate 104; (iii) attaching the femoral plate 114 to the femur 92; (iv) inserting the femoral rod 112 into the femur's medullary cavity through the femoral plate 114; (v) attaching the externally threaded member 120 to the tibial rod 102 with the first pin 125; (vi) threading the locking nut 130 and the internally threaded member 140 onto the externally threaded member 120; (vii) manipulating the leg to insert the cylindrical post 219 into the cylindrical recess 149; (viii) adjusting the externally threaded member 140 to a desired spacing; and (ix) inserting the second pin 145 to lock the femoral rod 112 to the internally threaded member 140. It will be appreciated that these steps do not all have to be performed in the order listed.

It should be appreciated that the present invention provides a modular system for a TKR assembly 100. In a current embodiment, a plurality of different-sized tibial plates, femoral plates, externally threaded members 120, and internally threaded members are provided to accommodate different patients and conditions. Similarly, the femoral and tibial rods may be provided in different lengths and with differing angular offsets.

Figure 9:
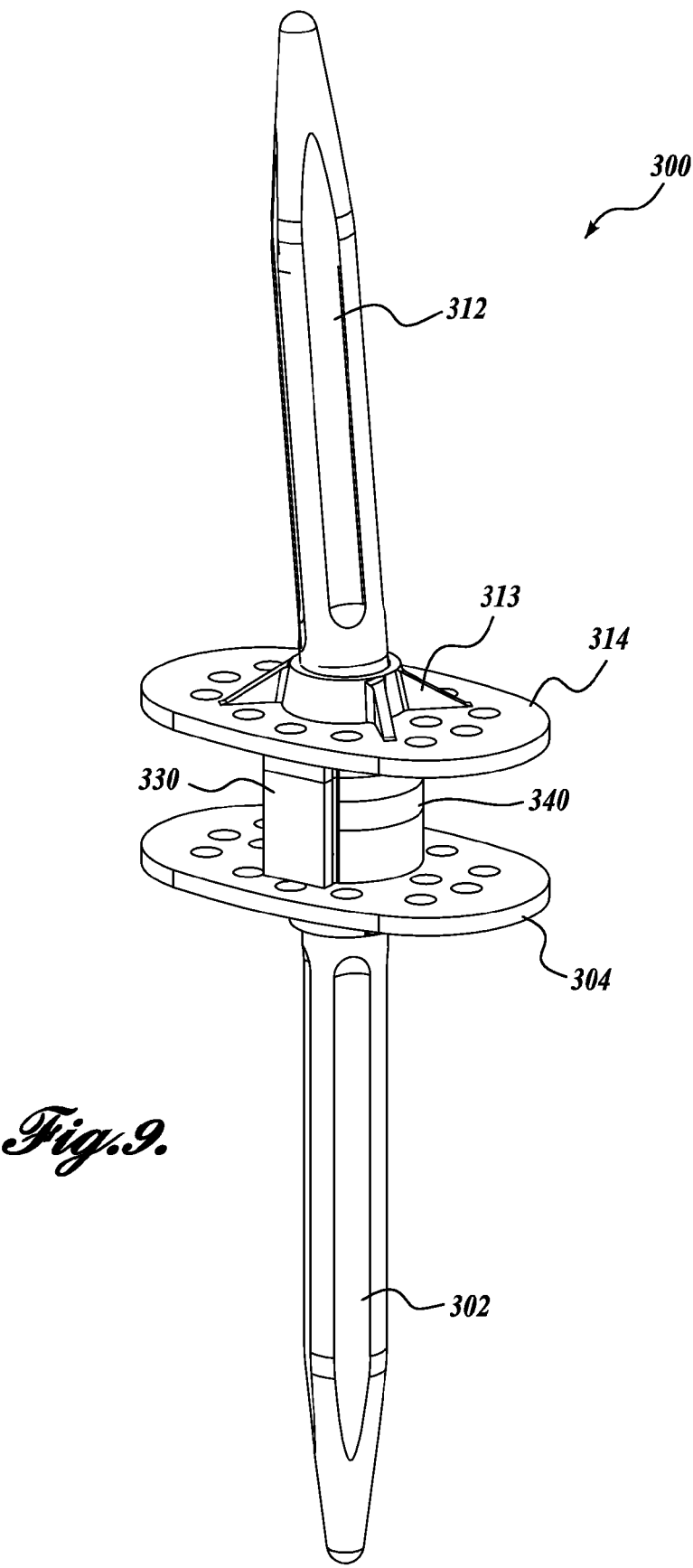
FIG. 9 is a perspective view of a second embodiment of a temporary knee replacement assembly in accordance with the present invention.
Figure 10:
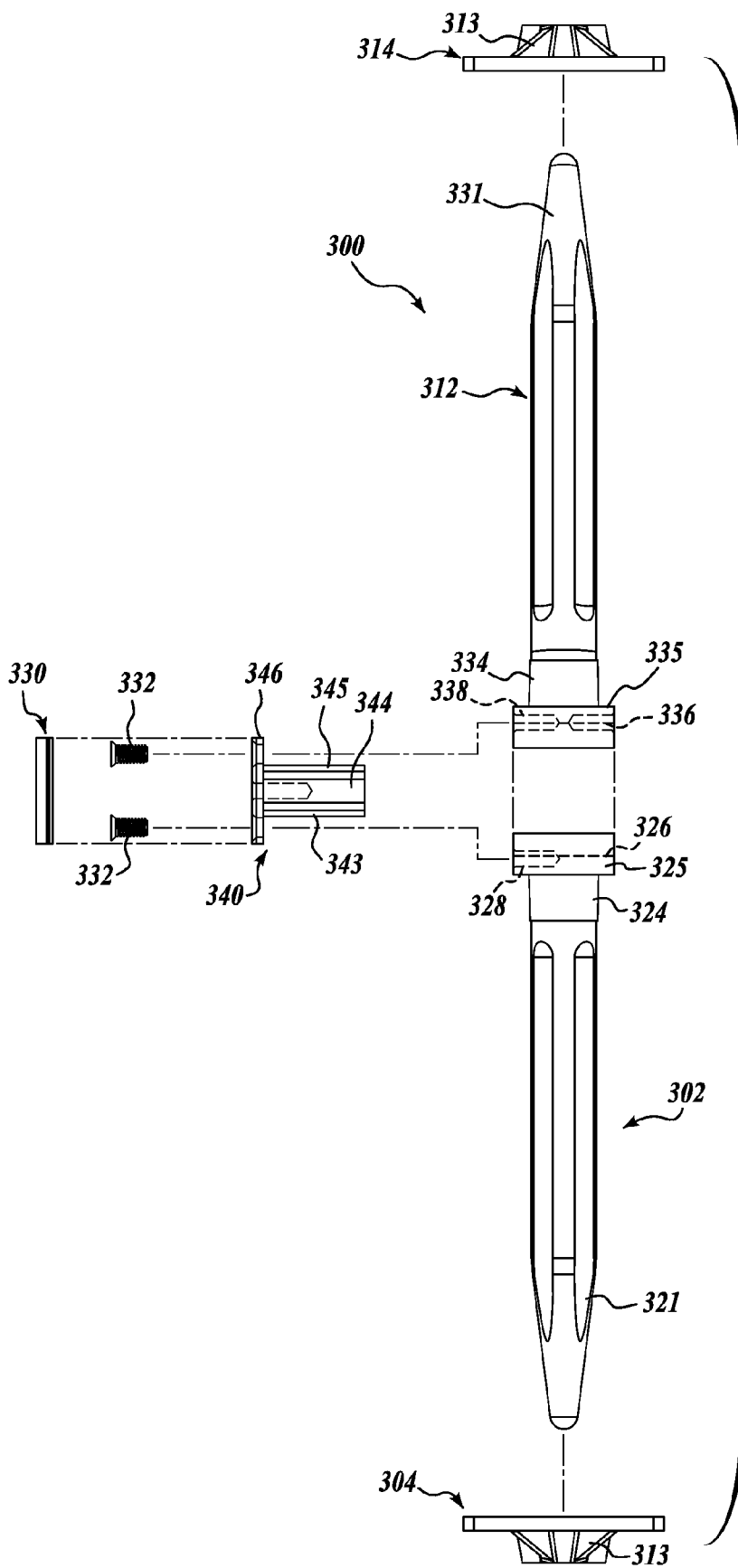
FIG. 10 is an exploded view of the temporary knee replacement assembly shown in FIG. 9.

A second embodiment of a TKR assembly 300 is shown assembled in FIG. 9, and in exploded view in FIG. 10. The TKR assembly 300 includes a tibial rod 302 that extends through a tibial plate 304 and is inserted deep into the tibial medullary cavity. Supports 313 formed on the tibial plate 304 engage the edge of the tibia medullary cavity. A femoral rod 312 extends through a corresponding femoral plate 314 into the femoral medullary cavity. Supports 313 formed on the femoral plate 314 engage the femur medullary cavity. The tibial rod 302 and femoral rod 312 are locked together, typically after they have been implanted in the respective medullary cavities, with a locking spacer 340 that slidably engages the rods 302, 312 and may be fixed in place with threaded fasteners 332.

In the current embodiment the tibial plate 304 is formed as a separate part from the tibial rod 302, and the femoral plate 314 is similarly formed as a separate part from the femoral rod 312. This modular construction has the advantage of providing flexibility customizing the TKR assembly 300 to the particular patient and situation. For example, a kit may be provided (an embodiment is discussed below) providing a plurality of the different components in different sizes. However, it will be readily apparent to persons of skill in the art that the tibial plate 304 and rod 302 may be formed as a single, unitary structure, and similarly the femoral plate 314 and rod 312 may be formed as a single, unitary structure. For example, in a kit form a plurality of rods with integral plates may be provided having differing lengths and plate dimensions.

Figure 11:
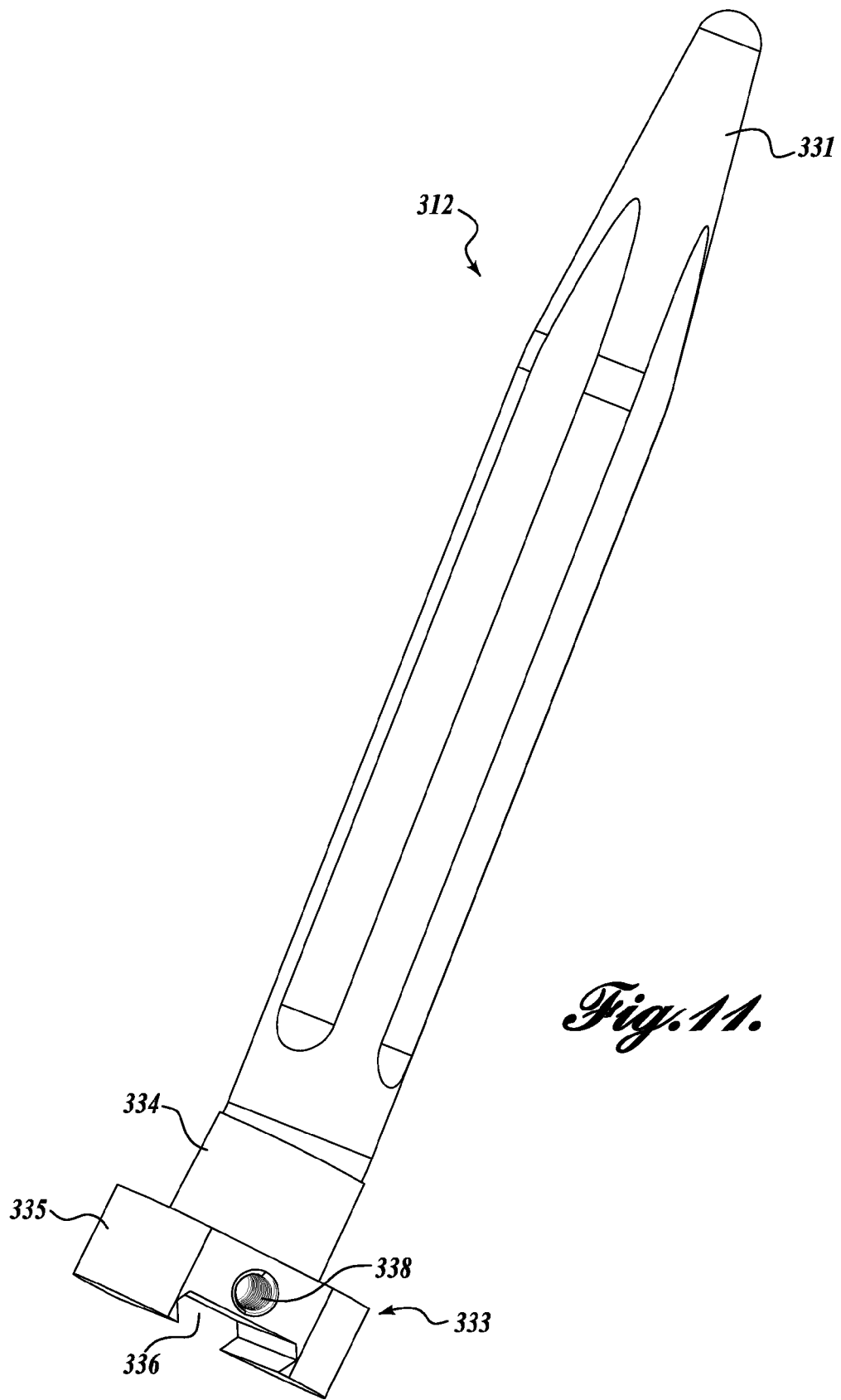
FIG. 11 is a perspective view of the femoral rod for the temporary knee replacement assembly shown in FIG. 9.

The femoral rod 312 is shown in isolation in FIG. 11 and includes an elongate portion 331 that is inserted into the medullary cavity. A head portion 333 includes a cylindrical post portion 334 that slidably receives the femoral plate 314, and an enlarged end portion 335 that forms a shoulder stop for the femoral plate 314. The end portion 335 has a C-shaped channel 336 defined on its distal face and a threaded aperture 338 configured to engage the corresponding threaded fastener 332 for securing the locking spacer 340 to the femoral rod 312. The elongate portion 331 is disposed at an angle relative to the post portion 334 and end portion 335, to accommodate the desired varus-valgus alignment.

The tibial rod 302 is similar to the femoral rod 312 (see FIG. 10) except the elongate portion 321 and proximal portions 324, 325 are typically aligned. The tibial rod 302 includes an elongate portion 321, a cylindrical post portion 324 that slidably receives the tibial plate 304, and an enlarged end portion 325. A C-shaped channel 326 extends across the distal face of the end portion 325 and is configured to be aligned with the C-shaped channel 336 on the femoral rod 312. A threaded aperture 328 is configured to threadably engage the other threaded fastener 332.

An advantage of the present system is that the femoral rod 312 may be positioned in the patient's femur medullary cavity independently of the tibial rod 302, so its rotational position is optimal. The tibial rod 302 is inserted into the tibia medullary cavity, and may be rotationally positioned such that the C-shaped channels 326, 336 are aligned.

Optionally, the rods 302, 312 and/or other components, may include an antibiotic or other antimicrobial coating, such as the antibiotic cement described above, silver plating, or the like. The antimicrobial agent or coating may be incorporated into the rods 302, 312 at the time of manufacture, for example plating or otherwise coating the rods with an antimicrobial metal, or a coating may be applied or molded onto the rods 302, 312 prior to surgery.

Figure 12:
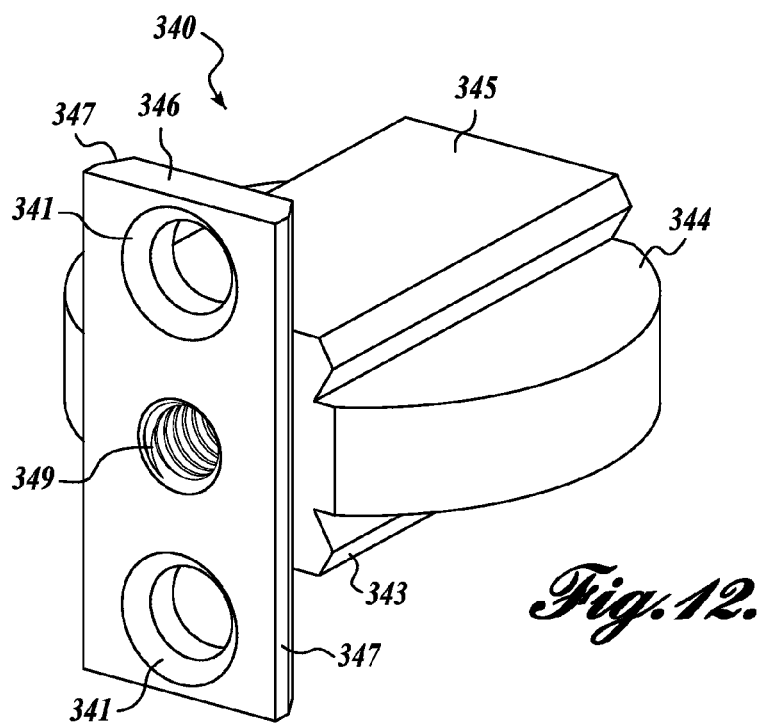
FIG. 12 is a perspective view of the locking spacer for the temporary knee replacement assembly shown in FIG. 9.

A perspective view of the locking spacer 340 is shown in FIG. 12. The locking spacer 340 includes a central spacing portion 344, a first C-shaped slide 343 that is sized and shaped to slidably engage the C-shaped channel 326 on the tibial rod 302, and a second C-shaped slide 345 that is sized and shaped to slidably engage the C-shaped channel 336 on the femoral rod 312. Therefore, when assembled as shown in FIG. 9, the tibial rod 302, locking spacer 340, and femoral rod 312 cooperatively define a very stable and secure elongate assembly configured to immobilize the patient's knee joint.

The locking spacer 340 includes an attachment plate 346 having oppositely disposed apertures 341 that are sized to slidably receive the fasteners 332 that attach the locking spacer 340 to the rods 302, 312. A center threaded aperture 349 is provided to facilitate removal of the locking spacer 340. For example, when the TKR assembly 300 is to be removed, a threaded tool (not shown) may be threaded into the aperture 349 and used to pull the locking spacer 340 out, thereby separating the rods 302, 312 to facilitate removal of the TKR ASSEMBLY 300.

Figure 13:
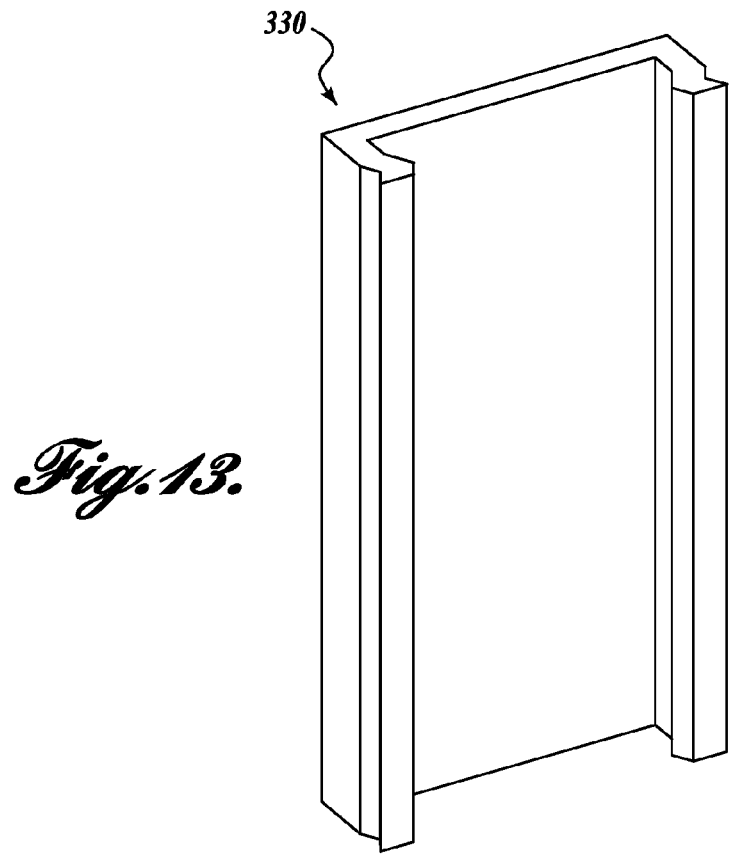
FIG. 13 is a perspective view of the cover for the temporary knee replacement assembly shown in FIG. 9.

The longitudinal edges 347 of the attachment plate 346 are preferably beveled or otherwise shaped to receive a snap-on cover 330 (see FIG. 10) that is shaped to be press-fit onto the attachment plate 346. FIG. 13 shows the snap-on cover 330 in isolation.

Figure 14:
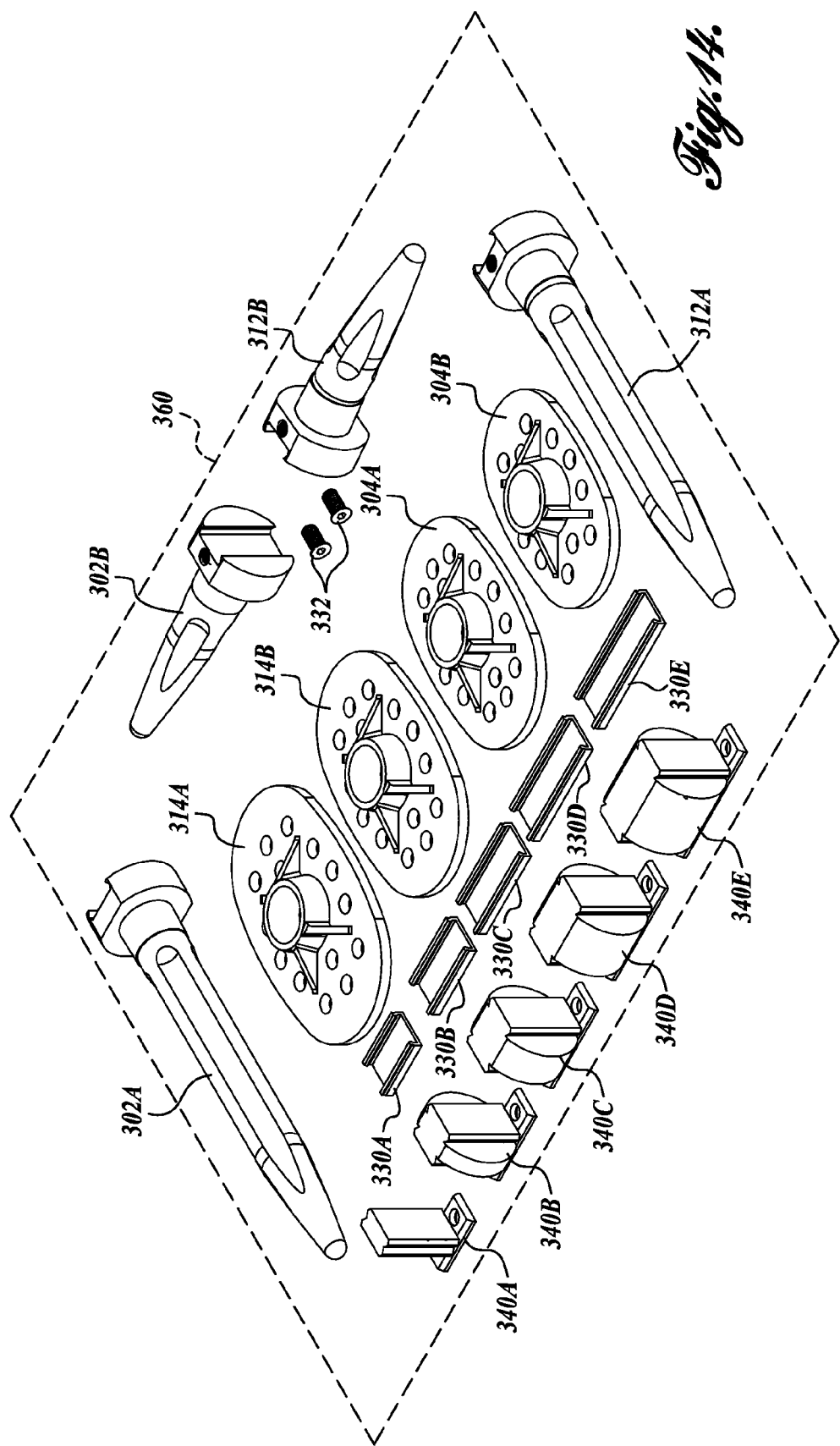
FIG. 14 illustrates a temporary knee replacement kit similar to the temporary knee replacement assembly shown in FIG. 9, and having a plurality of rods, plates, covers, and spacers.

As shown in FIG. 14, in one embodiment a kit 360 having components in a range of sizes may be provided, such that a surgeon may select the particular components most suitable for a particular patient situation. For example, the kit 360 may comprise a plurality of tibial rods 302A, 302B having differing lengths and a plurality of femoral rods 312A, 312B having differing lengths. Other dimensions of the rods may be varied also. For example, a kit may have a plurality of femoral rods having differing angular orientations of the elongate portions 331 and/or having differing transverse dimensions. The kit 360 may further include a plurality of tibial plates 304A, 304B and femoral plates 314A, 314B having different sizing. The kit 360 may also include a plurality of locking spacers 340A-340E having different longitudinal dimensions, with corresponding covers 330A-330E. The kit 360 provides the surgeon with the ability to select the most suitable components at the time of the operation and taking into consideration the observed condition of the knee.

In one sequence of installation of the TKR ASSEMBLY 300, after surgically preparing the knee for the TKR ASSEMBLY 300 and optionally applying an antibiotic cement into the medullary cavities, the surgeon selects the tibial plate 304 from a plurality of tibial plates based on the size of the tibia. It will be appreciated by persons of skill in the art that the tibial plate 304 (and the femoral plate 314) provides an advantage of helping to control the antibiotic cement (when used) by inhibiting the antibiotic cement from migrating out of the respective medullary cavities. The tibial rod 302 may be selected to have a length sufficient to provide the needed stability. The selected tibial 302 rod and plate 304 may be preassembled by inserting the rod 302 through the support aperture in the plate, such that the supports 313 are positioned to engage the tibia. Similarly, the femoral plate 314 and femoral rod 312 are selected and preassembled. The femoral rod 312 may be rotated such that the elongate portion 331 is oriented to match angle direction of the femur medullary cavity. The suitably sized spacer 340 is selected, and the second C-shaped slide 345 is slid into the C-shaped channel 336 on the femoral rod 312 and is fixed to the femoral rod 312 with the threaded fastener 332. The patient's lower leg is then manipulated to slide the first C-shaped slide 343 into the C-shaped channel 326 on the tibial rod 302, which is secured with the threaded fastener 332. The cover 330 corresponding with the selected spacer 340 is then snapped onto the attachment plate 346 to cover the threaded fasteners 332. Typically, an antibiotic cement or other antimicrobial treatment (not shown) is then applied about the joint. Optionally, an antibiotic cement may be applied directly to the rods 304, 314 prior to inserting them into the respective medullary cavities.

The disclosed TKR assemblies 100, 300 simplify the implantation and removal of the TKR assemblies, while still providing for the deep intra-medullary antimicrobial treatment of both the femur and the tibia, and providing for customizing the TKR implant to the needs of the particular patient. The tibial rod 302 and femoral rod 312 are separately implanted in the respective medullary cavities, and then joined to form a unitary assembly, minimizing the required manipulation of the patient's joint. The separation between the rods 302, 312 may be adjusted or selected during the surgery, to accommodate the particular needs of the particular joint. The kit 360 provides the surgeon with the flexibility to optimize the joint for the patient, taking into account any new information discovered during the surgery. The rods 302, 312 may then be readily separated when the TKR assembly 100, 300 is to be removed.

Currently, preferred embodiments of the present invention have been described to provide a better understanding of the invention through an exemplary embodiment, and the present invention is not intended to be limited by the current embodiment. Obvious variations in the present embodiment include reversing certain structural details of the femoral and tibial subassemblies, using other means for locking the femoral and temporal rods to the connecting hardware, including, for example, set screws, locking tabs, or the like. It is also contemplated that the invention may be practiced with straightforward modifications to provide an articulated joint, for example, by providing a hinging mechanism, or incorporating elements such at those disclosed in U.S. Pat. No. 8,097,039, incorporated by reference above.

In another embodiment, the present invention may be applied to providing an orthopedic implant for lengthening or spanning a section of missing bone intermediate along a long bone, for example as a fusion rod. For example, the implant may be used to replace an intermediate section of bone that had to be surgically removed, or as a temporary orthopedic support replacing a prior implant that has become infected, to provide antibiotic or other antimicrobial treatment prior to implanting a permanent replacement.

The embodiments of the invention in which an exclusive property or privilege is claimed are defined as follows:

1. A temporary knee replacement comprising:
   a tibial plate having an aperture therethrough;
   a tibial rod having an elongate portion configured to be inserted into a tibia medullary cavity, an intermediate post portion, and an end portion defining a first channel, wherein the elongate portion is configured to extend through the tibial plate aperture such that the end portion abuts the tibial plate;
   a femoral plate having an aperture therethrough;
   a femoral rod having an elongate portion configured to be inserted into a femur medullary cavity, an intermediate post portion, and an end portion defining a second channel, wherein the elongate portion is configured to extend through the femoral plate aperture such that the end portion abuts the femoral plate;
   a locking spacer comprising (i) a first slide portion that is shaped to slidably engage the first channel such that the first slide portion is restrained from moving within the first channel except along the first channel, (ii) a second slide portion that is shaped to slidably engage the second channel such that the second slide portion is restrained from moving within the second channel except along the second channel, and (iii) an attachment plate portion; and
   a first fastener configured to fix the position of the first slide portion in the first channel and a second fastener configured to fix the position of the second slide portion in the second channel, wherein the first fastener comprises a threaded fastener that extends through an aperture in the attachment plate portion and threadably engages a threaded aperture in the end portion of the tibial rod.

2. The temporary knee replacement of claim 1, wherein the tibial plate further comprises projections that extend from the tibial plate and are configured to engage the tibia.

3. The temporary knee replacement of claim 2, wherein the projections comprise tapered posts or a center support structure.

4. The temporary knee replacement of claim 1, wherein the first and second slide portions are C-shaped in cross section.

5. The temporary knee replacement of claim 1, further comprising a snap-on cover that is configured to engage the attachment plate portion of the locking spacer.

6. The temporary knee replacement of claim 1, wherein the locking spacer further comprises a threaded aperture that is configured to engage a threaded tool for removal of the locking spacer.

7. The temporary knee replacement of claim 1, wherein the elongate portion of the femoral rod further comprises an antimicrobial coating.

8. The temporary knee replacement of claim 7, wherein the antimicrobial coating is molded onto the elongate portion of the femoral rod.

9. The temporary knee replacement of claim 1, further comprising a plurality of locking spacers, wherein each of the plurality of locking spacers has a different longitudinal dimension such that the spacing between the tibial rod and the femoral rod is adjustable by selecting one of the plurality of locking spacers.

10. The temporary knee replacement of claim 1, wherein the temporary knee replacement is a non-articulated static spacer.

11. A temporary knee replacement kit comprising:
a plurality of tibial plates comprising a relatively larger tibial plate and a relatively smaller tibial plate, each tibial plate having an aperture therethrough;
a plurality of tibial rods comprising a relatively longer tibial rod and a relatively shorter tibial rod, wherein the tibial rods each have an elongate portion configured to be inserted into a medullary cavity, an intermediate post portion, and an end portion defining a lower transverse channel;
a plurality of femoral plates comprising a relatively larger femoral plate and a relatively smaller femoral plate, each femoral plate having an aperture therethrough;
a plurality of femoral rods comprising a relatively longer femoral rod and a relatively shorter femoral rod, wherein the femoral rods each have an elongate portion configured to be inserted into a medullary cavity, an intermediate post portion, and an end portion defining an upper transverse channel;
a plurality of locking spacers having different lengths, wherein each of the locking spacers comprise (i) a first slide that is configured to slidably engage the lower transverse channel of any of the plurality of tibial rods such that the first slide is restrained from moving within the lower transverse channel except along the lower transverse channel, (ii) a second slide that is shaped to slidably engage the upper transverse channel of any of the plurality of femoral rods such that the second slide is restrained from moving within the upper transverse channel except along the upper transverse channel, and (iii) an attachment plate; and
means for releasably fixing the attachment plate to any selected one of the plurality of tibial rods and means for releasably fixing the attachment plate to any selected one of the plurality of femoral rods;
wherein a temporary knee replacement assembly may be assembled using any one of the plurality of tibial plates, any one of the plurality of tibial rods, any one of the plurality of femoral plates, any one of the plurality of femoral rods, and any one of the plurality of locking spacers.

12. The temporary knee replacement kit of claim 11, wherein each of the plurality of tibial plates further comprise projections that are configured to engage the tibia to fix the location of the tibial plate.

13. The temporary knee replacement kit of claim 11, wherein the upper and lower transverse channels are C-shaped.

14. The temporary knee replacement kit of claim 11, further comprising a plurality of snap-on covers, each cover associated with one of the plurality of locking spacers, wherein each snap-on cover is configured to removably engage the attachment plate of the associated locking spacer.

15. The temporary knee replacement kit of claim 11 further comprising an antibiotic material comprising a mixture of an antibiotic, a bone cement powder, and a monomer.

16. A temporary knee replacement comprising:
a tibial component comprising an elongate rod configured to be inserted into a tibia medullary cavity and having a proximal end portion defining a first channel, the tibial component further comprising an outwardly-extending plate portion disposed between the elongate rod and the proximal end portion, wherein the plate portion is configured to engage a proximal end of the tibia;
a femoral component comprising an elongate rod configured to be inserted into a femur medullary cavity and having a distal end portion defining a second channel, the femoral component further comprising an outwardly-extending plate portion disposed between the elongate rod and the distal end portion, wherein the plate portion is configured to engage a distal end of the femur;
a locking spacer comprising (i) a first slide portion that is shaped to slidably engage the first channel such that the first slide portion is restrained from moving within the first channel except along the first channel, (ii) a second slide portion that is shaped to slidably engage the second channel such that the second slide portion is restrained from moving within the second channel except slidably along the second channel, and (iii) an attachment plate portion; and
a first fastener configured to fix the position of the first slide portion in the first channel and a second fastener configured to fix the position of the second slide portion in the second channel, wherein the first fastener comprises a threaded fastener that extends through an aperture in the attachment plate portion and threadably engages a threaded aperture in the end portion of the tibial rod.

17. The temporary knee replacement of claim 16, wherein the first and second slide portions are C-shaped in cross section.

18. A temporary knee replacement comprising:
a tibial plate having an aperture therethrough;
a tibial rod having an elongate portion configured to be inserted into a tibia medullary cavity, an intermediate post portion, and an end portion defining a first channel, wherein the elongate portion is configured to extend through the tibial plate aperture such that the end portion abuts the tibial plate;
a femoral plate having an aperture therethrough;
a femoral rod having an elongate portion configured to be inserted into a femur medullary cavity, an intermediate post portion, and an end portion defining a second channel, wherein the elongate portion is configured to extend through the femoral plate aperture such that the end portion abuts the femoral plate;
a locking spacer comprising (i) a first slide portion that is shaped to slidably engage the first channel such that the first slide portion is restrained from moving within the first channel except along the first channel, (ii) a second slide portion that is shaped to slidably engage the second channel such that the second slide portion is restrained from moving within the second channel except along the second channel, and (iii) an attachment plate portion, and wherein the first and second slide portions are C-shaped in cross section; and
a first fastener configured to fix the position of the first slide portion in the first channel and a second fastener configured to fix the position of the second slide portion in the second channel.

19. A temporary knee replacement comprising:
a tibial plate having an aperture therethrough;
a tibial rod having an elongate portion configured to be inserted into a tibia medullary cavity, an intermediate post portion, and an end portion defining a first channel, wherein the elongate portion is configured to extend through the tibial plate aperture such that the end portion abuts the tibial plate;
a femoral plate having an aperture therethrough;
a femoral rod having an elongate portion configured to be inserted into a femur medullary cavity, an intermediate post portion, and an end portion defining a second channel, wherein the elongate portion is configured to extend through the femoral plate aperture such that the end portion abuts the femoral plate;
a locking spacer comprising (i) a first slide portion that is shaped to slidably engage the first channel such that the first slide portion is restrained from moving within the first channel except along the first channel, (ii) a second slide portion that is shaped to slidably engage the second channel such that the second slide portion is restrained from moving within the second channel except along the second channel, and (iii) an attachment plate portion;
a first fastener configured to fix the position of the first slide portion in the first channel and a second fastener configured to fix the position of the second slide portion in the second channel; and
a snap-on cover that is configured to engage the attachment plate portion of the locking spacer.

* * * * *